United States Patent [19]

Fukushima et al.

[11] Patent Number: 5,041,592

[45] Date of Patent: Aug. 20, 1991

[54] ORGANIC SILICON COMPOUNDS, HYDROLYZATES THEREOF, AND RUBBER PLASTICIZERS

[75] Inventors: Motoo Fukushima; Jun Hatakeyama; Kunio Itoh, all of Annaka, Japan

[73] Assignee: Shin-Etsu Chemical Co., Ltd., Tokyo, Japan

[21] Appl. No.: 359,696

[22] Filed: May 31, 1989

[30] Foreign Application Priority Data

May 31, 1988 [JP] Japan .................................. 63-133500

[51] Int. Cl.$^5$ .............................. C07F 7/08; C07F 7/18
[52] U.S. Cl. .................................................. 556/438
[58] Field of Search ......................................... 556/438

[56] References Cited

U.S. PATENT DOCUMENTS

| | | | |
|---|---|---|---|
| 2,920,091 | 1/1960 | Black | 556/438 |
| 2,991,301 | 7/1961 | Schmidt | 556/438 |
| 3,271,331 | 9/1966 | Ender | 556/438 X |
| 4,701,277 | 10/1987 | Mohr et al. | 556/438 X |

OTHER PUBLICATIONS

Noll, "Chemistry and Technology of Silicones", Academic Press, N.Y. (1968), p. 197.

*Primary Examiner*—Paul F. Shaver
*Attorney, Agent, or Firm*—Birch, Stewart, Kolasch & Birch

[57] ABSTRACT

A novel organic silicon compound and hydrolyzate thereof are provided in which an alkoxysilane having an alkoxy radical attached to the silicon atom is attached to a polyester through an alkylene radical. They are useful as a plasticizer for rubber.

7 Claims, 2 Drawing Sheets

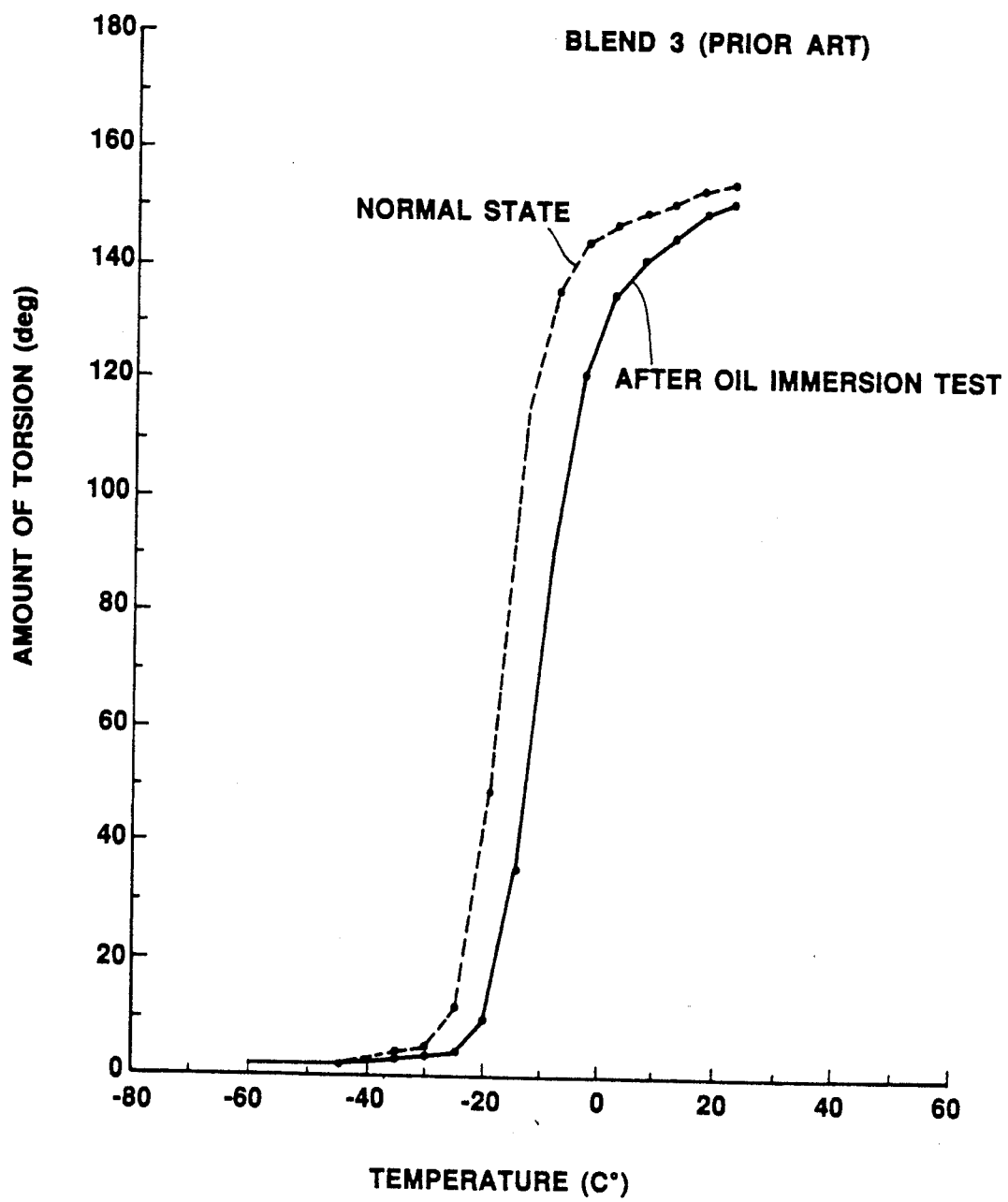

ORGANIC SILICON COMPOUNDS, HYDROLYZATES THEREOF, AND RUBBER PLASTICIZERS

BACKGROUND OF THE INVENTION

1. Field of the Invention

The present invention relates to novel organic silicon compounds, hydrolyzates thereof, and rubber plasticizers comprising the same. More particularly, it relates to novel organic silicon compounds and hydrolyzates thereof which are useful as rubber plasticizers having improved properties including low volatility, non-extractability, and thermal aging and low-temperature resistance improvements in combination with modern advanced rubber articles on which high performance demand is imposed.

2. Prior Art

In the prior art, polyester plasticizers are most often used with rubber articles. Such polyester plasticizers are generally liquid polyesters prepared by dehydration condensation between a double alcohol terminated glycol and an aliphatic monobasic acid, usually having a viscosity of about 10 to about 7,000 centipoise. They are widely used with synthetic rubbers such as acrylonitrile-butadiene rubbers (NBR), chloroprene rubbers (CR), acrylic rubbers (ACM and ANM) and fluoride rubbers (FKM) for providing plasticity and particularly, improved low-temperature resistance thereto.

However, during long term service of rubber articles in hot oil, these polyester plasticizers tend to be extracted with and migrate into hot oil, failing to take advantage of their low-temperature resistance improving facility. Extraction and migration of polyester plasticizers into hot oil may be somewhat controlled by increasing the molecular weight of polyester plasticizers at the expense of efficient plasticization and low-temperature resistance improvement.

Although the polyester plasticizers insure improved physical properties to vulcanized rubbers, their drawbacks are serious as described above. There is a need for a plasticizer which is non-extractable, efficient in plasticization, and effective in improving low-temperature resistance when used with rubber.

SUMMARY OF THE INVENTION

The present inventors have succeeded in producing a novel organic silicon compound having the formula:

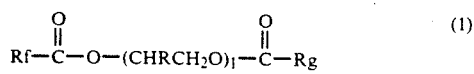
(1)

wherein Rf is $-(CH_2)m-SiR^1{}_{3-n}(OR^2)n$,
R is hydrogen or a methyl radical,
$R^1$ is a hydrogen atom or a monovalent hydrocarbon radical having 1 to 8 carbon atoms,
$R^2$ is a monovalent hydrocarbon radical having 1 to 8 carbon atoms,
Rg is a monovalent hydrocarbon radical having 1 to 20 carbon atoms or Rf,
letter l is an integer of from 2 to 15,
m is an integer of from 2 to 20, and
n is an integer of from 1 to 3, by effecting dehydration condensation between a polyethylene glycol and a double bond terminated fatty acid to form a polyether ester having a double bond at one or both ends, and effecting addition reaction of an alkoxysilane to the polyether ester. The present inventors have found that the novel organic silicon compound of formula (1) and its hydrolyzate are useful as rubber plasticizers.

When blended in a rubber composition as a plasticizer, the organic silicon compound of formula (1) or its hydrolyzate provides an improved plasticizing function as would be found with conventional polyester plasticizers, and imparts improved physical properties and low-temperature resistance to vulcanized rubber. Since the organic silicon compound of formula (1) is characterized in that an alkoxysilane having an alkoxy radical or radicals attached to the silicon atom is attached to a polyester through an alkylene radical, the alkoxy radical in its molecule is readily hydrolyzable to chemically bond with an inorganic material which is often blended in the rubber composition as a reinforcing filler, for example, silica, alumina, and clay. Because of this nature, the organic silicon compound of formula (1) is low volatile and non-extractable and undergoes no or little extraction or migration in hot oil. Thus rubber articles containing the organic silicon compound of formula (1) experience no or little lowering in physical properties and low-temperature resistance during long term service in hot oil.

As is known in the art, organic silicon compounds having a hydrolyzable alkoxy radical and one or more different functional radicals are used as the silane coupling agent. Nevertheless, it is the present inventors' own discovery that polyester plasticizers having an alkoxysilane incorporated through an alkylene radical are useful as the rubber plasticizer.

The present invention provides a novel organic silicon compound of formula (1) as defined above, a hydrolyzate thereof, and a rubber plasticizer comprising the organic silicon compound or hydrolyzate thereof.

BRIEF DESCRIPTION OF THE DRAWINGS

FIG. 2 is a diagram showing the amount of tortion vs. temperature in a low-temperature tortion test on the rubber sheet of prior art Blend 3.

DETAILED DESCRIPTION OF THE INVENTION

Figure 1:
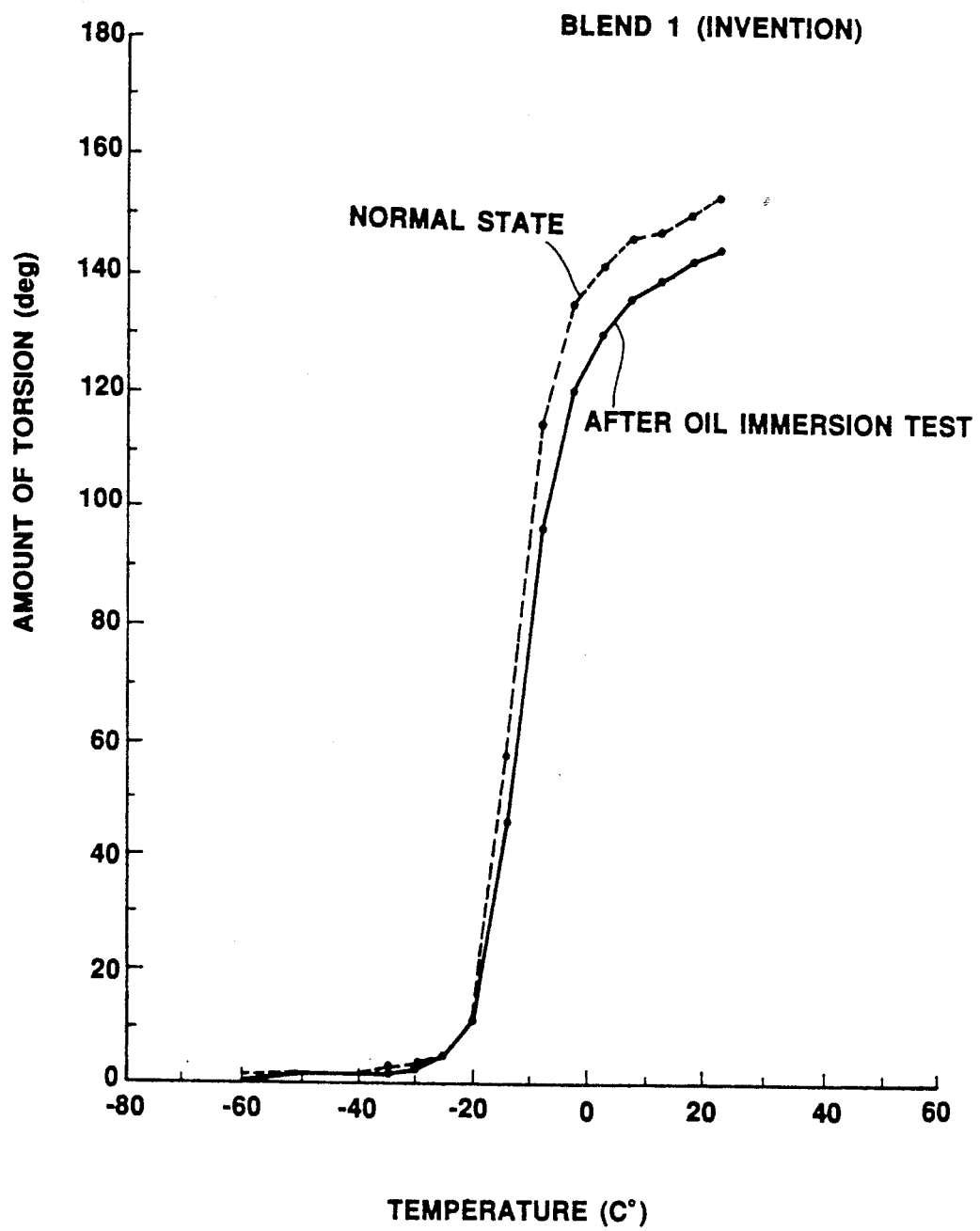
FIG. 1 is a diagram showing the amount of tortion vs. temperature in a low-temperature tortion test on the rubber sheet of Blend 1 according to the present invention.

The novel organic silicon compounds of the present invention have the formula:

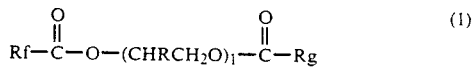
(1)

wherein R is hydrogen or a methyl radical, preferably hydrogen for heat resistance, and Rf is an alkoxysilane having an alkoxy radical in its molecule represented by $-(CH_2)_m-SiR^1{}_{3-n}(OR^2)n$.

In the alkoxysilane represented by Rf, $R^1$ is a hydrogen atom or a monovalent hydrocarbon radical having 1 to 8 carbon atoms, preferably a lower alkyl radical having 1 to 5 carbon atoms, such as a methyl and ethyl radical; $R^2$ is a monovalent hydrocarbon radical having 1 to 8 carbon atoms, preferably a lower alkyl radical having 1 to 5 carbon atoms, such as a methyl and ethyl radical; and letter m is an integer of from 2 to 20, preferably from 3 to 10; and n is an integer of from 1 to 3.

In formula (1), letter 1 is an integer of from 2 to 15, preferably from 2 to 10, and Rg is a monovalent hydrocarbon radical having 1 to 20 carbon atoms or an alkoxysilylalkyl radical as defined for Rf. The $C_1$-$C_{20}$ monovalent hydrocarbon radicals represented by Rg may preferably be straight chain or branched alkyl radicals including methyl, ethyl, propyl, butyl, pentyl, hexyl, heptyl, octyl, isopropyl, and dimethylhexyl radicals.

The novel organic silicon compounds of formula (1) may be prepared by the following process.

First, dehydration condensation is effected between a polyethylene glycol and a fatty acid having a double bond at a terminal to form a polyether ester having a double bond at one or both ends. The polyethylene glycol used herein may preferably have an average molecular weight of about 100 to about 600. Polyethylene glycols having an average molecular weight of more than 600 are less desirable because they are oily or waxy and compounds of formula (1) prepared from such polyethylene glycols have a likelihood of lowering low-temperature resistance when blended in rubber as the plasticizer.

The double bond terminated fatty acids used herein may preferably be aliphatic monocarboxylic acids having 2 to 20 carbon atoms, more preferably 3 to 11 carbon atoms, in an acid residue moiety and terminated with a double bond. Examples are acrylic acid, vinyl acetic acid, 4-pentenoic acid, 5-hexenoic acid, 2,2-dimethyl-3-butenoic acid, 9-decenoic acid, and 10-undecenoic acid. They are commercially available from reagent manufacturers, for example, Aldrich Chemical Co., Inc. Among the double bond terminated fatty acids, acrylic acid whose fatty acid residue has 2 carbon atoms might invite difficulty in the subsequent ester synthesis since it tends to polymerize during ester synthesis because of too high reactivity of its double bond. Fatty acids whose fatty acid residue has more than 20 carbon atoms would often result in organic silicon compounds which are less effective in improving low-temperature resistance when blended in rubber compositions. The double bond terminated fatty acids may be used alone or in admixture of two or more.

The fatty acid is reacted with the polyethylene glycol to form a polyether ester having a double bond at one or both ends. More particularly, a polyether ester having a double bond at both ends is prepared by reacting one mol of fatty acid with ½ mol of polyethylene glycol. A polyether ester having a double bond only at one end may preferably be prepared by using a mixture of a fatty acid terminated with a double bond and a double bond-free fatty acid in a molar ratio of 1:1 and reacting one mol of the fatty acid mixture with ½ mol of polyethylene glycol.

The double bond-free fatty acids used in the latter are preferably aliphatic saturated monocarboxylic acids whose fatty acid residue has 1 to 20 carbon atoms, more preferably 2 to 11 carbon atoms. Examples include acetic acid, propionic acid, lactic acid, valerianic acid, caproic acid, heptanoic acid, caprylic acid, pelargonic acid, capric acid, n-undecylenic acid, lauric acid, n-tridecylic acid, myristic acid, n-pendadecylic acid, palmitic acid, margaric acid (heptadecanoic acid), stearic acid, n-nonadecylic acid, arachidic acid, isolactic acid, isovalerianic acid, pivalic acid, isocaproic acid, β-methylvalerianic acid, methyl isopropylacetic acid, and 1,5-dimethylhexane-1-carboxylic acid. Among others, branched fatty acids are preferred from the point of view of low-temperature resistance improvement, for example, such as isolactic acid, isovalerianic acid, pivalic acid, isocaproic acid, β-methylvalerianic acid, methyl isopropylacetic acid, and 1,5-dimethylhexane-1carboxylic acid.

The dehydration condensation between polyethylene glycol and fatty acid as defined above may be carried out in a conventional manner, for example, in an organic solvent capable of azeotropic dehydration such as toluene, benzene, and xylene in the presence of an acid catalyst such as sulfuric acid. For example, reaction is carried out at 110° to 120° C. for about 2 to about 6 hours in the case of toluene solvent to effect azeotropic dehydration at or near the boiling point of the solvent for esterification.

Next, an alkoxysilane having an alkoxy radical in its molecule is added to the resulting organic solvent solution of the polyether ester having a double bond at one or both ends. Addition reaction takes place between the polyether ester and the alkoxysilane, producing the end compound of formula (1).

The alkoxysilane used herein is not particularly limited. The preferred alkoxysilanes are represented by the formula: $HSiR^1{}_{3-n}(OR^2)n$ wherein $R^1$, $R^2$, and n are as defined above. Among them, trimethoxysilane, methyldimethoxysilane, and triethoxysilane are preferred. The most preferred alkoxysilane is trimethoxysilane. The alkoxysilane is added to the polyether ester in equimolar amounts.

The addition reaction may be completed by heating at 60° to 120° C. for about 1 to about 6 hours, typically for about 2 hours under reflux, the reaction mixture in an organic solvent such as toluene, benzene, and xylene in the presence of a catalyst such as chloroplatinic acid, typically H2PtCl6. The end compound of formula (1) is then obtained in approximately quantitative yields.

The present invention also provides hydrolyzates of the organic silicon compounds of formula (1) as described earlier. The hydrolyzate may be obtained, for example, by introducing the organic silicon compound of formula (1) in a hydrous alcohol, typically an isopropyl alcohol/water mixture (50/50 wt%) for hydrolysis in the presence of a weak acid catalyst such as about 1% by weight of acetic acid or about 0.1% by weight of hydrochloric acid. In such a situation, hydrolysis promptly proceeds at room temperature within about 2 to about 6 hours.

The organic silicon compounds and hydrolyzates thereof are useful as rubber plasticizers. When blended in rubber compositions, the organic silicon compounds and hydrolyzates thereof are not only low volatile, non-extractable, and effective in plasticizing the rubber, but also allow the vulcanized rubber to maintain good physical properties and to exhibit improved low-temperature properties and thus improved low-temperature resistance.

The organic silicon compounds and hydrolyzates thereof may be blended as a plasticizer in a variety of rubber stock materials including natural rubber and synthetic rubbers such as styrene-butadiene rubber, isoprene rubber, chloroprene rubber, acrylonitrile-butadiene rubber, acrylic rubber, silicone rubber, and fluoride rubber, generally in amounts of about 1 to about 30% by weight, preferably about 5 to about 15% by weight of the rubber stock material as are conventional plasticizers.

Any desired additives may be added to rubber compositions having the organic silicon compounds and hydrolyzates thereof incorporated therein as a plasticizer as is usually the case with ordinary rubber compositions. Examples of the useful additives include vulcanizing agents such as sulfur compounds, organic peroxides, and metal oxides, usually in amounts of 0.1 to 5% by weight; vulcanizing accelerators such as metal oxides, fatty acids, e.g., stearic acid and derivatives thereof, usually in amounts of 0.5 to 10% by weight; antioxidants such as diphenylamine derivatives and naphthylamines; inorganic and organic reinforcing fillers such as carbon black, clay, alumina, and silica; other plasticizers (e.g., conventional polyester plasticizers); coloring agents; and flame retarders.

When blended in rubber compositions, the organic silicon compounds and hydrolyzates thereof according to the present invention provide improved plasticity to the rubber compositions and allow the vulcanized rubber to exhibit good physical properties and improved low-temperature properties, particularly improved low-temperature resistance. They are low volatile and non-extractable since little or no extraction or migration thereof in hot oil takes place upon exposure of rubber articles to hot oil, meaning that the once improved plasticity and low-temperature resistance are never lost. The organic silicon compounds and hydrolyzates thereof are very useful as rubber plasticizers.

EXAMPLES

Examples of the present invention are given below by way of illustration and not by way of limitation.

EXAMPLE 1

The reaction scheme used in this example is shown below.

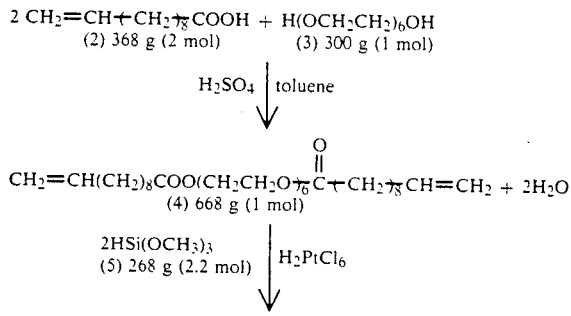

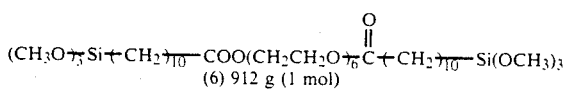

A 3-liter flask equipped with an ester condenser was charged with 300 grams of polyethylene glycol of formula (3) having an average molecular weight of 300 (Toho Polyethylene Glycol #300, manufactured by Toho Chemical Industry K.K., to be abbreviated as PEG, hereinafter), 368 grams of 10-undecenoic acid of formula (2) having a molecular weight of 184 (manufactured by Aldrich Chemical Co., Inc., to be abbreviated as UA, hereinafter) and 600 grams of toluene. With stirring, 0.6 grams (0.1% by weight) of $H_2SO_4$ was added to the flask and the mixture was heated under reflux in a nitrogen stream. Heating was interrupted when water resulting from dehydration condensation was recovered in the theoretical amount (36 grams). The reaction solution was then allowed to cool down. To the reaction solution were added excess 5 grams of $NaHCO_3$ for neutralization and then 12 grams of activated carbon (Shirasagi C, manufactured by Mochida Pharmaceutical K.K.). Filtration gave a toluene solution containing 668 grams of the ether ester compound of formula (4).

To the toluene solution was added 0.1 gram of an isopropanol solution containing 1% by weight of $H_2PtCl_6$. The solution was heated at 90° C before 268 grams of trimethoxysilane of formula (5) having a molecular weight of 122 (LS-330, manufactured by Shin-Etsu Chemical Co., Ltd.) was slowly added dropwise. Thereafter, the solution was heated under reflux for 2 hours, completing the reaction. The solution was stripped under vacuum of the excess LS-330 and toluene, obtaining the end product, ether ester compound of formula (6) in a quantitative yield (912 grams).

The ether ester compound of formula (6) was measured for various physical properties and NMR spectrum, with the results shown below.

Viscosity: 65 centipoise at 25° C.
$D_{25}$: 0.99.
$n_D^{20}$: 1.4501.
NMR ($CDCl_3$): $\delta 0.97$ (4H, $SiCH_2$—), 1.38 (32H, $SiCH_2$—$(CH_2)_3$—), 2.33 (4H, $(CH_2)_8$—$CH_2COO$), 3.62 (18H, $Si(OCH_3)_3$), 3.71 (16H, —$(CH_2CH_2O)_4$—), 3.73 (4H, $COOCH_2CH_2O$—).

EXAMPLE 2

The reaction scheme used in this example is shown below.

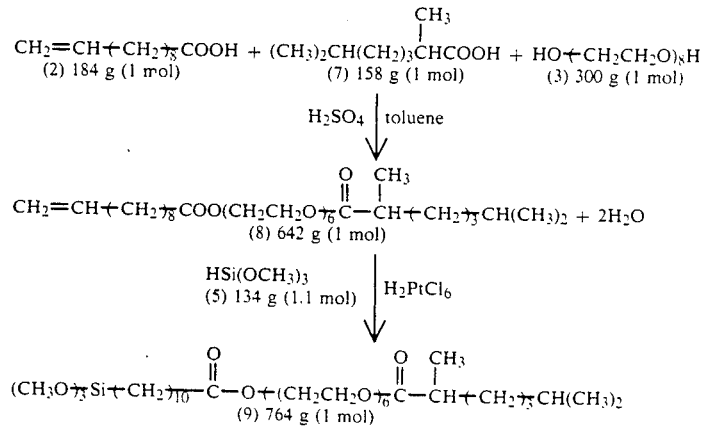

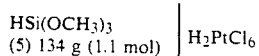

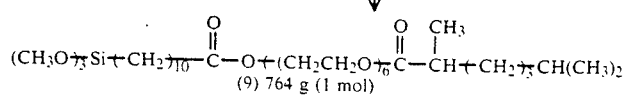

The procedure of Example 1 was repeated except that 158 grams of 1,5-dimethylhexane-1-carboxylic acid (abbreviated as DHA) of formula (7) having an average molecular weight of 158 which was synthesized by reducing citral followed by dehydration and oxidative cleavage of its double bonds according to the teaching of U.S. Pat. No. 2,417,220 was added to 184 grams of UA which was one half of the amount used in Example 1 and the amount of trimethoxysilane LS-330 was reduced to one half (134 grams) of the amount used in Example 1. An ether ester compound of formula (9) having a trimethoxysilyl radical at one end was obtained in an approximately quantitative yield (764 grams).

The ether ester compound of formula (9) was measured for physical properties and NMR spectrum, with the results shown below.

Viscosity: 45 centipoise at 25° C.
$D_{25}$: 1.00.
$n_D^{20}$: 1.4500
NMR (CDCl$_3$): $\delta$0.97 (2H, SiCH$_2$—), 1.00 (9H, (CH$_3$)$_2$CH(CH$_2$)$_3$(CH$_3$)CH—), 1.53 (7H, (CH$_3$)$_2$—CH(CH$_2$)$_3$(CH$_3$)CH—), 1.38 (16H, SiCH$_2$—(CH$_2$)$_8$—), 2.33 (3H, —CH$_2$COO—, —CH—COO—), 3.62 (9H, (CH$_3$O)$_3$Si—), 3.71 (16H, —(CH$_2$CH$_2$O)$_4$—), 3.73 (4H, —COOCH$_2$CH$_2$—O—), 4.21 (4H, —COOCH$_2$CH$_2$—O—).

EXAMPLE 3

This example is for comparison. The reaction scheme used in this comparative example is shown below.

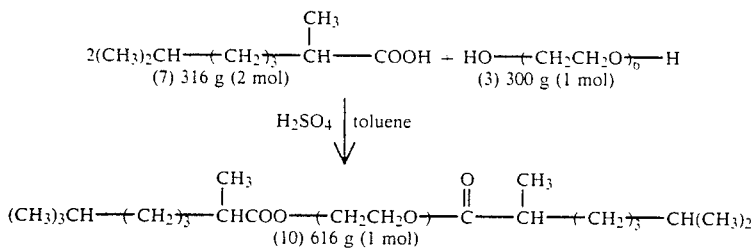

Reaction was carried out by a similar procedure to Example 1 by introducing 316 grams of DHA of formula (7) and 300 grams of PEG of formula (3) into toluene and adding H$_2$SO$_4$ catalyst thereto. An ether ester compound of formula (10) free of a trimethoxyxilyl radical at either end was obtained in a quantitative yield (616 grams).

The ether ester compound of formula (10) was measured for physical properties and NMR spectrum, with the results shown below.

Viscosity: 38 centipoise at 25° C.
$D_{25}$: 1.00.
$n_D^{20}$: 1.4494.
NMR (CDCl$_3$): $\delta$1.00 (18H, (CH$_3$)$_2$CH—(CH$_2$)$_3$(CH$_3$)CHCOOH), 1.53 (14H, (CH$_3$)$_2$—CH—(CH$_2$)$_3$—), 2.33 (2H, —(CH$_3$)$_2$CH—(CH$_2$)$_3$CH$_3$CHCOO—), 3.71 (16H, —(CH$_2$CH$_2$O)$_4$—), 3.73 (4H, —COOCH$_2$CH$_2$—O—), 4.21 (4H, —COOCH$_2$CH$_2$—O—).

BLEND EXAMPLES

A rubber blend having the composition shown in Table 1 containing the above-prepared compound of formula (6), (9) or (10) was milled in a twin roll mill and then heat pressed into a rubber sheet at 165° C for 12 minutes.

The rubber sheet thus molded was post vulcanized at 180° C. for 8 hours. The vulcanized rubber sheet in normal state was measured for various properties by commonly used methods. The properties measured are hardness Hs according to JIS K-6301, percent elongation E, tensile strength Ts (kg/cm$^2$), tear strength T$_{RA}$ (kg/cm), percent volume change $\Delta$V (%), and percent weight change $\Delta$W. The low-temperature resistance of the sample was evaluated by carrying out a Gehman tortion test under the conditions described below to measure the specific modulus according to JIS K6301.

An oil immersion test was carried out by immersing the rubber sheet in engine oil (Nissan Super SD5W-30) at 175° C. for 70 hours for heat extraction. At the end of the test, the sample was measured for the same properties and low-temperature resistance as above.

Gehman tortion test

Coolant: ethyl alcohol.
Wire type: 0.500 gram.f-cm/°.
T2, T5, T10, T100: temperatures at which tortional modulus is 2, 5, 10 and 100 times that at room temperature (20° C.). T2 = —8.8° C.,
T5 = —3.1° C.,
T10 = —5.7° C.,
T100 = —23.8° C.
The results are shown in Table 2.
The tortion test data for Blend Nos. 1 and 3 are plotted in FIGS. 1 and 2.

TABLE 1

| Ingredients, parts by weight | Composition | | |
|---|---|---|---|
| | Blend 1 | Blend 2 | Blend 3* |
| Hycor 4042*1 | 100 | 100 | 100 |
| Nipsil VN3Lp*2 | 50 | 50 | 50 |
| Stearic acid | 1 | 1 | 1 |
| Naugard 445*3 | 2 | 2 | 2 |
| Plasticizer | 10 | 10 | 10 |
| compound formula | (6) | (9) | (10) |
| MgO | 4 | 4 | 4 |
| PZ*4 | 1.2 | 1.2 | 1.2 |
| Trithiocyanuric acid Zisnet F*5 | 1.2 | 1.2 | 1.2 |

*Blend 3 is outside the scope of the invention
*1acrylic rubber (manufactured by B. F. Goodrich)
*2silica (manufactured by Nihon Aerosil K.K.)
*34,4'-bis(4-α,α-dimethylbenzyl)diphenylamine antioxidant (manufactured by Uniroyal Co.)
*4zinc dimethyldithiocarbamate (Nocceler PZ, manufactured by Ohuchi Shinkoh K.K.)
*5Zisnet F (manufactured by Sankyo Kasei K.K.):

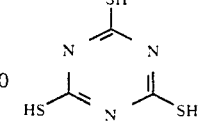

TABLE 2

| | Blend 1 | Blend 2 | Blend 3* |
|---|---|---|---|
| Normal state | | | |
| Properties | | | |
| Hs | 77 | 74 | 73 |

TABLE 2-continued

| | Blend 1 | Blend 2 | Blend 3* |
|---|---|---|---|
| E (%) | 365 | 360 | 345 |
| Ts (kg/cm$^2$) | 130 | 133 | 134 |
| T$_{RA}$ (kg/cm) | 47 | 47 | 47 |
| Specific modulus | | | |
| T2 (°C.) | −9.2 | −11.8 | −12.7 |
| T5 (°C.) | −13.3 | −16.5 | −17.2 |
| T10 (°C.) | −16.2 | −18.8 | −19.5 |
| T100 (°C.) | −25.8 | −27.9 | −28.1 |
| After oil immersion test Properties | | | |
| Hs | 67 | 70 | 76 |
| E (%) | 365 | 370 | 355 |
| Ts (kg/cm$^2$) | 131 | 128 | 130 |
| ΔV (%) | +8.0 | +2.4 | +0.5 |
| ΔW (%) | +5.1 | +0.4 | −0.4 |
| Specific modulus | | | |
| T2 (°C.) | −8.6 | −8.7 | −5.5 |
| T5 (°C.) | −13.3 | −14.5 | −9.8 |
| T10 (°C.) | −16.4 | −18.2 | −12.0 |
| T100 (°C.) | −26.0 | −27.7 | −19.3 |
| Roll milling Roll stick | no | slight | marked |

As seen from the results of Table 2 and FIGS. 1 and 2, rubber sheets having the organic silicon compound of the invention incorporated as a plasticizer have good physical properties and improved low-temperature resistance while experiencing no substantial loss in such properties and resistance upon immersion in hot oil for a long term. It is demonstrated that the organic silicon compounds of the invention are useful rubber plasticizers since they impart sufficient plasticity and improved low-temperature resistance and are low volatile and non-extractable when blended in rubber compositions.

We claim:

1. An organic silicon compound having the formula:

wherein Rf is $-(CH_2)_m-SiR^1{}_{3-n}(OR^2)_n$,
R is hydrogen or a methyl radical,
R$^1$ is a hydrogen atom or a monovalent hydrocarbon radical having 1 to 8 carbon atoms,
R$^2$ is a monovalent hydrocarbon radical having 1 to 8 carbon atoms,
Rg is a monovalent hydrocarbon radical having 1 to 20 carbon atoms or Rf,
letter l is an integer of from 2 to 15,
m is an integer of from 2 to 20, and
n is an integer of from 1 to 3.

2. The organic silicon compound as set forth in claim 1 wherein R is hydrogen.

3. A hydrolyzate of an organic silicon compound as set forth in claim 1 or 2.

4. The organic silicon compound as set forth in claim 1 wherein R$^2$ is a lower alkyl radical having 1 to 5 carbon atoms, letter l is an integer of from 2 to 10, and m is an integer of from 3 to 10.

5. The organic silicon compound as set forth in claim 1 wherein Rg is a radical selected from the group consisting of methyl, ethyl, propyl, butyl, pentyl, hexyl, heptyl, octyl, isopropyl and dimethylhexyl.

6. The hydrolyzate of an organic silicon compound as set forth in claim 4.

7. The hydrolyzate of an organic silicon compound as set forth in claim 5.

* * * * *